United States Patent
Guillon et al.

(10) Patent No.: US 9,505,681 B2
(45) Date of Patent: Nov. 29, 2016

(54) PROCESS FOR ISOMERIZING AN AROMATIC C8 CUT IN THE PRESENCE OF A CATALYST BASED ON AN EUO ZEOLITE AND A PARTICULAR SODIUM CONTENT

(71) Applicant: IFP Energies nouvelles, Rueil-Malmaison (FR)

(72) Inventors: Emmanuelle Guillon, Vourles (FR); Laure Brandhorst, Lyons (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 381 days.

(21) Appl. No.: 14/077,242

(22) Filed: Nov. 12, 2013

(65) Prior Publication Data

US 2014/0135550 A1 May 15, 2014

(30) Foreign Application Priority Data

Nov. 15, 2012 (FR) ..................... 12/03064

(51) Int. Cl.

| | |
|---|---|
| C07C 5/27 | (2006.01) |
| C07C 15/08 | (2006.01) |
| B01J 29/74 | (2006.01) |
| B01J 21/04 | (2006.01) |
| B01J 23/42 | (2006.01) |
| B01J 23/44 | (2006.01) |
| B01J 23/58 | (2006.01) |
| B01J 37/00 | (2006.01) |

(52) U.S. Cl.
CPC .............. *C07C 5/2775* (2013.01); *B01J 21/04* (2013.01); *B01J 23/42* (2013.01); *B01J 23/44* (2013.01); *B01J 23/58* (2013.01); *B01J 29/7446* (2013.01); *B01J 37/0009* (2013.01); *C07C 2521/04* (2013.01); *C07C 2529/74* (2013.01); *Y02P 20/52* (2015.11)

(58) Field of Classification Search
CPC .. C07C 5/2775; C07C 15/08; B01J 29/7446; B01J 37/0009; B01J 21/04; B01J 23/42; B01J 23/44; B01J 23/58
See application file for complete search history.

(56) References Cited

U.S. PATENT DOCUMENTS 6,057,486 A * 5/2000 Merlen ................ B01J 29/7246
502/64

\* cited by examiner

*Primary Examiner* — In Suk Bullock
*Assistant Examiner* — Jason Chong
(74) *Attorney, Agent, or Firm* — Millen White Zelano and Branigan, PC; Csaba Henter; Anthony Zelano

(57) ABSTRACT

A process for isomerizing an aromatic cut containing at least one aromatic compound containing eight carbon atoms per molecule, which includes bringing the aromatic cut into contact with a catalyst containing a zeolite with structure type EUO, which catalyst has been prepared by obtaining a zeolite with structure type EUO having an overall Si/Al atomic ratio in the range 5 to 45, a sodium content in the range 500 to 5000 ppm by weight, with a Na/Al ratio in the range 5% to 20% by mole, and thereafter performing the following:
i) preparing a support by shaping the zeolite with a matrix such that the zeolite content is in the range 8% to 15% by weight with respect to the support;
ii) depositing at least one metal from group VIII of the periodic classification of the elements onto the support or onto the zeolite;
wherein the catalyst contains a final sodium content of 75 to 600 ppm by weight.

19 Claims, No Drawings

PROCESS FOR ISOMERIZING AN AROMATIC C8 CUT IN THE PRESENCE OF A CATALYST BASED ON AN EUO ZEOLITE AND A PARTICULAR SODIUM CONTENT

FIELD OF THE INVENTION

The present invention relates to the isomerization of an aromatic cut containing at least one aromatic compound containing eight carbon atoms per molecule with a view to the production of xylenes. Said aromatic cut envisaged in the present invention is a feed containing a mixture of xylenes, ethylbenzene or a mixture of xylenes and ethylbenzene. This feed is conventionally known as an "aromatic C8 cut".

More particularly, the present invention relates to a process for isomerizing an aromatic feed comprising at least one aromatic compound containing eight carbon atoms per molecule with a view to maximizing the production of para-xylene, by means of a zeolitic catalyst with a controlled sodium content.

PRIOR ART

Catalysis of the isomerization of ethylbenzene into xylenes necessitates the presence of a group VIII metal. Optimized formulations based on mordenite and a group VIII metal result in catalysts with which unwanted side reactions are still non-negligible. An example which can be cited is naphtha ring opening, followed or otherwise by cracking, or dismutation and transalkylation reactions of C8 aromatics, which result in the formation of unwanted aromatics. Thus, the discovery of novel, more selective catalysts is of particular interest.

Zeolites used for the isomerization of aromatic C8 cuts include ZSM-5, used alone or as a mixture with other zeolites such as mordenite, for example. Those catalysts have been described in particular in U.S. Pat. No. 4,467,129, U.S. Pat. No. 4,482,773 and EP-B-0 013 617. Other catalysts, principally based on mordenite, have been described, for example, in U.S. Pat. No. 4,723,051, U.S. Pat. No. 4,665,258 and FR-A-2 477 903. More recently, a catalyst based on a zeolite with structure type EUO has been proposed (EP-A1-923 987). Patent application WO-A-2005/065380 describes the use of a zeolite with structure type MTW for the isomerization of xylenes and ethylbenzene.

In formulations based on zeolite and in particular with structure type EUO, the alkali cation, in particular sodium, is normally eliminated at least in part and preferably almost completely, and thus the zeolite is almost completely in its protonic form with a Na/Al ratio of less than 2% by mole.

It has surprisingly been discovered that a catalyst in the form of extrudates or beads comprising at least one zeolite with structure type EUO, at least one matrix and at least one metal from group VIII of the periodic classification of the elements and containing a particular sodium content leads to improved catalytic performances in terms of activity when it is used in a process for the isomerization of an aromatic cut comprising at least one aromatic compound containing eight carbon atoms per molecule.

BRIEF DESCRIPTION OF THE INVENTION

The present invention concerns a process for the isomerization of an aromatic cut containing at least one aromatic compound containing 8 carbon atoms per molecule, comprising bringing said cut into contact with a catalyst containing a zeolite with structure type EUO, said catalyst having been prepared in accordance with a process comprising at least the following steps:

i) using at least one zeolite with structure type EUO having an overall Si/Al atomic ratio in the range 5 to 45, a sodium content in the range 500 to 5000 ppm by weight, with a Na/Al ratio in the range 5% to 20% by mole;

ii) preparing a support by shaping said zeolite with a matrix such that the zeolite content is in the range 8% to 15% by weight with respect to the support;

iii) depositing at least one metal from group VIII of the periodic classification of the elements onto said support or onto said zeolite;

the order of carrying out said steps ii) and iii) being immaterial following said step i), such that the catalyst contains a final sodium content in the range 75 to 600 ppm by weight.

Advantageously, in accordance with the invention, the zeolite with structure type EUO used in step i) has a Si/Al ratio in the range 10 to 40, preferably in the range 10 to 25.

Advantageously, in accordance with the invention, the catalyst contains a final sodium content in the range 150 to 500 ppm by weight.

Advantageously, in accordance with the invention, the zeolite with structure type EUO used in step i) has a sodium content in the range 1000 to 3500 ppm by weight with a Na/Al ratio in the range 5% to 15% by mole.

Advantageously, in accordance with the invention, the zeolite with structure type EUO used in step i) is obtained by synthesis or is purchased commercially.

Advantageously, in accordance with the invention, when said EUO zeolite used in step i) does not initially have a sodium content in the range 500-5000 and a Na/Al ratio in the range 5% to 20% by mole as required for step i), said EUO zeolite initially undergoes one or more ion exchange(s) in order to obtain the characteristics required in step i). In such a case, the ion exchange(s) is(are) advantageously carried out on the pre-calcined zeolite with structure type EUO.

Advantageously, in accordance with the invention, said zeolite with structure type EUO is EU-1 zeolite, ZSM-50 zeolite or TPZ-3 zeolite; more preferably, said zeolite with structure type EUO is EU-1 zeolite.

Advantageously, in accordance with the invention, the matrix is selected from clays, magnesia, aluminas, silicas, titanium oxide, boron oxide, zirconia, aluminium phosphates, titanium phosphates, zirconium phosphates, silica-aluminas and charcoal or a mixture of at least two of these compositions; more preferably, the matrix is an alumina.

Advantageously, in accordance with the invention, the matrix contains sodium in a sodium content of less than 2000 ppm, preferably less than 200 ppm.

Advantageously, in accordance with the invention, the catalyst also comprises at least one metal selected from metal from groups IIIA and IVA of the periodic classification of the elements.

Advantageously, in accordance with the invention, step ii) for shaping the support is followed by oven drying carried out at a temperature in the range 100° C. to 150° C. for a period in the range 5 to 20 hours followed by calcining carried out at a temperature in the range 250° C. to 600° C. for a period in the range 1 to 8 hours. Advantageously, in accordance with the invention, before carrying out the isomerization process, catalyst preparation is terminated by calcining at a temperature in the range 250° C. to 600° C. for a period in the range 0.5 to 10 hours preceded by drying at a temperature from ambient temperature to 250° C.

Advantageously, in accordance with the invention, prior reduction of the catalyst is carried out ex situ or in situ in a stream of hydrogen at a temperature of 450° C. to 600° C., for a period of 0.5 to 4 hours before carrying out the isomerization process.

Advantageously, in accordance with the invention, the isomerization process of the invention is carried out with a feed known as an aromatic cut comprising either only a mixture of xylenes or only ethylbenzene or a mixture of xylene(s) and ethylbenzene.

Advantageously, in accordance with the invention, the isomerization process is carried out at a temperature of 300° C. to 500° C., a partial pressure of hydrogen of 0.3 to 1.5 MPa, a total pressure of 0.45 to 1.9 MPa, and at an hourly space velocity, expressed in kilograms of feed introduced per kilogram of catalyst per hour, of 0.25 to 30 $h^{-1}$.

DETAILED DESCRIPTION OF THE INVENTION

Zeolite

The various zeolites with structure type EUO used in the process of the invention may be prepared by synthesis, or they may be of commercial origin.

Preferably, the various zeolites with structure type EUO used in the process of the invention are prepared by synthesis.

The zeolites EU-1, TPZ-3 and ZSM-50 with structure type EUO are well known in the art (Atlas of Zeolite Framework Types, Ch. Baerlocher, W. M. Meier, D. H. Olson, 5th edition, 2001). It is known that a zeolite with structure type EUO, in particular an EU-1 zeolite, has a one-dimensional microporous framework with a pore diameter of 4.1×5.4 Å (1 Å=1 Angström=$10^{-10}$ m). On the other hand, in an article in the review Zeolites (1988, 8, 74), N. A. Briscoe et al. showed that such one-dimensional channels have side pockets with a depth of 8.1 Å and a diameter of 6.8×5.8 Å.

The mode of preparation of said zeolites with structure type EUO is also well known to the skilled person. In general, the methods for preparing such zeolites comprise mixing a source of silicon, a source of aluminium, a source of an alkali metal and a particular organic nitrogen-containing compound, acting as a template, in an aqueous medium.

EU-1 zeolite, described in European patent application EP-A-0 042 226, is prepared using either an alkylated derivative of a polymethylene α-γ diammonium or a degradation product of said derivative, or again precursors of said derivative, as the template. TPZ-3 zeolite, described in European patent application EP-A-0 051 318, is prepared using the same template family as that employed for the synthesis of EU-1 zeolite. In particular, the use of the compound 1,6-N,N,N,N',N',N'-hexamethylhexamethylene-diammonium is described.

ZSM-50 zeolite, described in documents EP 0 159 845 and U.S. Pat. No. 4,640,829, is prepared using the dibenzyldimethylammonium (DBDMA) derivative as the template.

In addition, in order to carry out the preparation of the zeolite with structure type EUO used in said step i) and present in the catalyst employed in the isomerization process of the invention, the skilled person will usefully make reference to one or other of the references cited above describing the preparation of such zeolites.

More precisely, for the preparation of an EU-1 zeolite used in step i), the following are mixed in an aqueous medium: at least one source of silicon, at least one source of aluminium, at least one organic nitrogen-containing template Q with formula $R_1R_2R_3$—$N^+$—$(CH_2)_n$—$N^+$—$R_4R_5R_6$, in which n is in the range 3 to 12, the groups $R_1$ to $R_6$, which may be identical or different, are alkyl groups containing 1 to 8 carbon atoms, up to five of said groups $R_1$ to $R_6$ possibly being hydrogen, and optionally zeolitic seeds.

The reaction mixture has the following molar composition:

| | |
|---|---|
| $SiO_2/Al_2O_3$ | 10-150 |
| $OH^-/SiO_2$ | 0.1-6 |
| $(M^+ + Q)/Al_2O_3$ | 0.5-100 |
| $Q/(M^+ + Q)$ | 0.1-10 |
| $H_2O/SiO_2$ | 1-100, |

Q being the cation $R_1R_2R_3$—$N^+$-$(CH_2)_n$—$N^+$—$R_4R_5R_6$, described above, preferably 1,6 N,N,N,N',N',N'-hexamethylhexamethylene diammonium, and $M^+$ being an alkali or ammonium cation.

Said reaction mixture is reacted under autogenous pressure, optionally with a makeup of a gas, for example nitrogen, at a temperature in the range 85° C. to 250° C. until crystals of EU-1 zeolites are formed. The reaction period is in the range 1 minute to several months depending on the composition of the reagents, the mode of heating and of mixing, the temperature of the reaction and stirring. At the end of the reaction, the solid phase is collected on a filter and washed. At this stage, the EU-1 zeolite is known as as-synthesized and contains at least the cation $R_1R_2R_3$—$N^+$—$(CH_2)_n$—$N^+$—$R_4R_5R_6$, preferably 1,6 N,N,N,N',N',N'-hexamethylhexamethylene diammonium, in its intra-crystalline porosity.

In accordance with the invention, irrespective of whether it is of commercial origin or obtained by synthesis, said EUO zeolite used in step i) has an overall Si/Al atomic ratio in the range 5 to 45, preferably in the range 10 to 40 and more preferably in the range 10 to 25, a sodium content in the range 500 to 5000 ppm by weight and a Na/Al ratio in the range 5% to 20% by mole, preferably a sodium content in the range 1000 to 3500 ppm by weight, with a Na/Al ratio in the range 5% to 15% by mole.

The overall Si/Al atomic ratio determined by X ray fluorescence or atomic absorption, takes into account both the aluminium atoms present in the zeolitic framework and the aluminium atoms possibly present outside said zeolitic framework, also known as extra-framework aluminium.

Calcining

The zeolite used in step i) is advantageously calcined before carrying out step ii) or iii) of the invention. This calcining is advantageously carried out in dry air with a flow rate of gas in the range 1 L/h/g of zeolite to 5 L/h/g of solid. The temperature profile for calcining comprises 1 to 10 constant temperature stages lasting 30 min to 5 hours with temperature ramp-ups between them which may be in the range 0.5° C./min to 10° C./min, the final constant temperature stage being carried out between 400° C. and 700° C. for a period in the range 4 h to 3 days.

The treatment by calcining zeolite with structure type EUO of said step i) has the primary aim of eliminating the organic template present in the micropores of said zeolite, for example the cation $R_1R_2R_3$—$N^+$—$(CH_2)_n$—$N^+$—$R_4R_5R_6$, preferably 1,6 N,N,N,N',N',N'-hexamethylhexamethylene diammonium, when the zeolite synthesized during said step i) is EU-1 zeolite.

Ion Exchange

In accordance with the invention, when said EUO zeolite obtained by synthesis or purchased commercially used in step i) does not initially have a sodium content and a Na/Al ratio as required by the invention, said zeolite advantageously initially undergoes one or more ion exchange(s) in order to obtain an EUO zeolite with a sodium content and a Na/Al ratio as required by the invention. The ion exchange(s) can eliminate at least part of the alkali cation, in particular sodium, which may be present in the cationic position in the zeolite obtained by synthesis or from a commercial origin.

Advantageously, the ion exchange(s) is(are) carried out on the pre-calcined EUO zeolite.

In a variation of the process, when said EUO zeolite obtained by synthesis or purchased commercially used in step i) does not initially have the required sodium content and Na/Al ratio for the invention, an equivalent solution would be to carry out the ion exchange(s) on the support of step ii), i.e. on the zeolite shaped with the matrix. Said support is advantageously pre-calcined.

An aqueous solution of ammonium nitrate $NH_4NO_3$, ammonium acetate $CH_3COONH_4$, tetrapropylammonium hydroxide $C_{12}H_{27}NO$, tetramethylammonium hydroxide $C_4H_{13}NO$ or tetraethylammonium hydroxide $C8H_{21}NO$ with a normality in the range 0.2 to 12N may be used to carry out the exchange. The ratio between the volume of the aqueous solution used to carry out the exchange (mL) and the mass of zeolite or dry support to be exchanged (g) is in the range 2 to 20, preferably in the range 5 to 15. The solid is poured into a flask or an Erlenmeyer in which is an aqueous solution with the ammonium precursor. The mixture is stirred and optionally heated to a temperature in the range 50° C. to 150° C. for a period in the range 2 to 10 hours. The solution is then removed and the solid is rinsed with distilled water 2 to 10 times then oven dried at a temperature in the range 60° C. to 130° C. for a period in the range 1 hour to 24 hours. The solid obtained is dried and is then calcined in a quartz reactor provided with a frit in the middle, with gas moving from bottom to top. Beneath the frit, the lower portion is filled with carborundum in order to preheat the gases before they pass over the solid.

The exchange is followed by calcining, which takes place in air, preferably dry, with a gas flow rate in the range 1 L/h/g of solid to 5 L/h/g of solid. The calcining temperature profile includes 3 to 10 constant temperature stages with temperature ramp-ups between them which may be at 1° C./min to 10° C./min; the final constant temperature stage is carried out between 400° C. and 700° C. for a period in the range 1 to 10 hours.

In the case in which step iii) is carried out before step ii) and said EUO zeolite obtained by synthesis or purchased commercially used in step i) does not have the required sodium content and Na/Al ratio of the invention, step iii) is carried out on the EUO zeolite which has initially undergone one or more ion exchange(s) so as to obtain the required characteristics of the invention.

The ion exchange(s) is(are) carried out on said EUO zeolite, which has preferably already been calcined, so as to obtain an EUO zeolite with the characteristics required in step i): a sodium content in the zeolite in the range 500 to 5000 ppm by weight with a Na/Al ratio in the range 5% to 20% by mole; preferably, a sodium content in the range 1000 to 3500 ppm by weight with a Na/Al ratio in the range 5% to 15% by mole.

Preparation of Support

Preparation of the catalyst comprising a zeolite with structure type EUO for the purposes of using it in the isomerization process of the invention is continued by carrying out said step ii) for shaping a support comprising at least one matrix and at least one EUO zeolite.

Step iii) for depositing at least one metal from group VIII of the periodic classification of the elements of the invention may be carried out on the zeolite or on the support. Thus, the order for carrying out said steps ii) and iii) following said step i) is immaterial. Preferably, said step ii) precedes said step iii).

In order to carry out said step ii) for preparing the support by shaping said zeolite with structure type EUO, preferably EU-1 zeolite, a matrix is used which is selected from clays, magnesia, aluminas, silicas, titanium oxide, boron oxide, zirconia, aluminium phosphates, titanium phosphates, zirconium phosphates, silica-aluminas and charcoal or a mixture of at least two of these compositions. Preferably, the matrix is an alumina.

The quantity of zeolite in the support is in the range 8% to 15% by weight. During preparation of the support, the matrix used to shape the zeolite may contain sodium; preferably, it has a sodium content of less than 2000 ppm, preferably less than 200 ppm.

In the case in which the matrix contains sodium, the sodium content of the support or the catalyst in the invention is taken to be equal to the sum of the sodium content of the zeolite and the sodium content of the matrix.

Advantageously, the support, i.e. the zeolite associated with the matrix, is shaped into beads or extrudates, preferably into extrudates.

The preparation of the support in accordance with said step ii) more particularly consists of mixing the zeolite with structure type EUO, preferably EU-1 zeolite, in a moist matrix gel, preferably alumina, generally obtained by mixing at least one acid and a matrix powder for the period necessary to obtain good homogeneity in the paste, i.e. for about ten minutes, for example, then passing the paste obtained through a die in order to form extrudates, for example with a diameter of 0.4 to 4 mm.

Drying and Calcining the Support

Shaping of the support impregnated with at least one metal in accordance with the invention or otherwise is generally followed by drying then by calcining. Drying is advantageously carried out at a temperature in the range 100° C. to 150° C. for a period in the range 5 to 20 hours in an oven.

Calcining is advantageously carried out at a temperature in the range 250° C. to 600° C. for a period in the range 1 to 8 hours.

Preparation of Catalyst

Step iii) for preparing the catalyst comprising a zeolite with structure type EUO, preferably an EU-1 zeolite, consists of depositing at least one metal from group VIII of the periodic classification of the elements and optionally at least one metal selected from metal from groups IIIA, IVA and VIIB. This deposition is advantageously carried out on the zeolite of step i), preferably previously calcined, or on the support of step ii), preferably already calcined.

Said metal from group VIII present in the catalyst used in the isomerization process of the invention is selected from iron, cobalt, nickel, ruthenium, rhodium, palladium, osmium, iridium and platinum, preferably from the noble metals and highly preferably from palladium and platinum. Still more preferably, said metal from group VIII is platinum. In accordance with the method carried out for depositing said metal from group VIII, as indicated below in the description, said metal from group VIII, preferably platinum, may be deposited preponderantly on the zeolite or on the matrix.

Said metal selected from metal from groups IIIA, IVA and VIIB and possibly present in the catalyst used in the isomerization process of the invention is selected from gallium, indium, tin and rhenium, preferably from indium, tin and rhenium.

The catalyst used in the isomerization process of the invention may be prepared using any method known to the skilled person.

Preferably, following calcining carried out at the end of step ii) on the support, at least one metal from group VIII is introduced onto the support, namely either primarily onto the matrix or primarily onto the zeolite, or onto the zeolite-matrix assembly. Said metal is advantageously deposited on the support using the dry impregnation technique or the excess impregnation technique. When several metals are introduced, these may be introduced either all in the same manner or using different techniques.

Any precursors of the group VIII metals are suitable for depositing one or more metal(s) from group VIII onto the support. In particular, for any noble group VIII metal, it is possible to use ammonium compounds or compounds such as, for example, ammonium chloroplatinate, platinum dicarbonyl dichloride, hexahydroxyplatinic acid, palladium chloride or palladium nitrate. The platinum is generally introduced in the form of hexachloroplatinic acid. The noble group VIII metal is preferably introduced by impregnation using an aqueous or organic solution of one of the metallic compounds cited above. Examples of organic solvents which may be cited are paraffinic, naphthenic or aromatic hydrocarbons containing 6 to 12 carbon atoms per molecule, for example, and halogenated organic compounds containing 1 to 12 carbon atoms per molecule, for example. Examples which may be cited are n-heptane, methylcyclohexane, toluene and chloroform. It is also possible to use mixtures of solvents.

Controlling certain of the parameters involved in deposition, in particular the nature of the precursor of the metal(s) from group VIII used, means that deposition of said metal(s) can be directed to be primarily on the matrix or on the zeolite.

Thus, in order to introduce the group VIII metal(s), preferably platinum and/or palladium, mainly onto the matrix, it is possible to carry out an anion exchange with hexachloroplatinic acid and/or hexachloropalladic acid, in the presence of a competing agent, for example hydrochloric acid. This deposition is preferably followed by calcining, for example at a temperature in the range 350° C. to 550° C., and for a period in the range 1 to 4 hours. With such precursors, the group VIII metal(s) is/are deposited mainly onto the matrix and said metal(s) are properly dispersed and have good macroscopic distribution through the catalyst grain.

It is also possible to envisage depositing the group VIII metal(s), preferably platinum and/or palladium, by cationic exchange such that said metal(s) are deposited mainly onto the zeolite. Thus, in the case of platinum, the precursor may, for example, be selected from: ammonium compounds such as tetrammine platinum (II) salts with formula $Pt(NH_3)_4X_2$, hexammine platinum (IV) salts with formula $Pt(NH_3)_6X_4$; halogenopentammine platinum (IV) salts with formula $(PtX(NH_3)_5)X_3$; N-tetrahalogenodiammine platinum salts with formula $PtX_4(NH_3)_2$; and halogenated compounds with formula $H(Pt(acac)_2X)$; X being a halogen selected from the group formed by chlorine, fluorine, bromine and iodine, X preferably being chlorine, and "acac" representing the acetylacetonate group (with empirical formula $C_5H_7O_2$), a derivative of acetylacetone. With such precursors, the group VIII metal(s) is/are deposited mainly on the zeolite and said metal(s) have good dispersion and good macroscopic distribution through the catalyst grain.

Dry impregnation of the metal from group VIII onto the support results in depositing said metal both on the matrix and on the zeolite.

In the case in which the catalyst used in the isomerization process of the invention also contains at least one additional metal selected from metals from groups IIIA, IVA and VIIB, any of the techniques for depositing such a metal which are known to the skilled person and any precursors of said metals may be suitable.

It is possible to add the group VIII metal(s) and that (those) from groups IIIA, IVA and VIIB either separately or simultaneously in at least one unitary step. When at least one metal from groups IIIA, IVA and VIIB is added separately, it is preferably added after the metal from group VIII.

The additional metal selected from metals from groups IIIA, IVA and VIIB may be introduced via compounds such as chlorides, bromides or nitrates of metals from groups IIIA, IVA and VIIB, for example. As an example, in the case of indium, the nitrate or chloride is advantageously used and in the case of rhenium, perrhenic acid is advantageously used. In the case of tin, the tin chlorides $SnCl_2$ and $SnCl_4$ are preferred. The additional metal selected from metals from groups IIIA, IVA and VIIB may also be introduced in the form of at least one organic compound selected from the group constituted by complexes of said metal, in particular polyketone complexes of the metal, and hydrocarbyl metals such as metal alkyls, cycloalkyls, aryls, alkylaryls and arylalkyls. In this latter case, the metal is advantageously introduced using a solution of an organometallic compound of said metal in an organic solvent. It is also possible to use organohalogen compounds of the metal. Particular examples of organic metal compounds which may be cited are tetrabutyltin, in the case of tin, and triphenylindium in the case of indium.

If the additional metal selected from metal from groups IIIA, IVA and VIIB is introduced before the metal from group VIII, the IIIA, IVA and/or VIIB metal compound used is generally selected from the group constituted by the metal halide, nitrate, acetate, tartrate, carbonate and oxalate. The introduction is advantageously carried out in aqueous solution. However, it may also be introduced with the aid of a solution of an organometallic metal compound, for example tetrabutyltin. In this case, before proceeding to introducing at least one metal from group VIII, calcining in air is carried out.

In addition, intermediate treatments such as calcining and/or reduction, for example, may be applied between successive depositions of the various metals.

Advantageously, before carrying out the isomerization process of the invention, preparation of the catalyst of the invention is generally terminated by calcining, usually at a temperature in the range 250° C. to 600° C., for a period in the range 0.5 to 10 hours, preferably preceded by drying, for example oven drying, at a temperature from ambient temperature to 250° C., preferably in the range 40° C. to 200° C. Said drying step is preferably carried out as the temperature is being raised to carry out said calcining.

Prior ex situ or in situ reduction of the catalyst may be carried out in a stream of hydrogen, for example at a temperature of 450° C. to 600° C., for a period of 0.5 to 4 hours, before carrying out the isomerization process.

Said metal(s) from group VIII is (are) advantageously deposited such that the dispersion of said metal(s), determined by chemisorption, is 50% to 100%, preferably 60% to 100%, more preferably 70% to 100%. Said metal(s) from group VIII is (are) also advantageously deposited so as to obtain good distribution of said metal(s) in the shaped catalyst. This distribution is characterized by its profile obtained using a Castaing microprobe. The ratio of concentrations of each element from group VIII in the core of the grain with respect to the edge of that same grain, defined as the distribution coefficient, is advantageously 0.7:1 to 1.3:1, preferably 0.8:1 to 1.2:1.

The metals from group VIII, preferably platinum, deposited on the zeolite and/or on the matrix, represent 0.01% to 4%, preferably 0.05% to 2% by weight with respect to the weight of catalyst. The matrix constitutes the complement to 100%.

When said catalyst contains at least one metal selected from metals from group IIIA, IVA and VIM, the quantity thereof may be up to 2% by weight with respect to the catalyst weight. It is thus advantageously 0.01% to 2%, preferably 0.05% to 1.0% by weight. When said catalyst contains sulphur, the content thereof may be such that the ratio of the number of sulphur atoms to the number of atoms of metal from group VIII deposited is up to 2:1. It is then advantageously 0.5:1 to 2:1.

In the case in which the catalyst contains no sulphur, reduction of the metal in hydrogen is advantageously carried out in situ before injecting the feed.

In the case in which the catalyst used in the invention contains sulphur, the sulphur is introduced onto the shaped, calcined catalyst containing the metal or metals cited above, either in situ prior to the catalytic reaction, or ex situ. Any type of sulphurization is carried out after reduction. In the case of in situ sulphurization, if the catalyst has not already been reduced, reduction is carried out before sulphurization. In the case of ex situ sulphurization, reduction is carried out followed by sulphurization. The sulphurization is carried out in the presence of hydrogen using any sulphurizing agent which is well known to the skilled person, such as dimethyl sulphide or hydrogen sulphide, for example. As an example, the catalyst is treated with a feed containing dimethyl sulphide in the presence of hydrogen, in a concentration such that the sulphur/metal atomic ratio is 1.5. The catalyst is then kept at approximately 400° C. in a flow of hydrogen for approximately 3 hours before injecting the feed.

The isomerization process of the invention consists of bringing an aromatic cut containing at least one aromatic compound containing eight carbon atoms per molecule into contact with at least said catalyst containing at least said zeolite with structure type EUO, preferably said EU-1 zeolite, said catalyst having been prepared in accordance with each of said steps i), ii) and iii) described above in the present description.

Feed

Said aromatic cut containing at least one aromatic compound containing eight carbon atoms per molecule advantageously comprises either solely a mixture of xylenes, or solely ethylbenzene, or a mixture of xylene(s) and ethylbenzene. Said isomerization process of the invention is advantageously carried out under the following operating conditions:

a temperature of 300° C. to 500° C., preferably 320° C. to 450° C. and more preferably 340° C. to 430° C.;

a partial pressure of hydrogen of 0.3 to 1.5 MPa, preferably 0.4 to 1.2 MPa and more preferably 0.7 to 1.2 MPa;

a total pressure of 0.45 to 1.9 MPa, preferably 0.6 to 1.5 MPa; and an hourly space velocity, expressed as kilograms of feed introduced per kilogram of catalyst per hour, of 0.25 to 30 $h^{-1}$, preferably 1 to 10 $h^{-1}$ and more preferably 2 to 6 $h^{-1}$.

The following examples illustrate the invention without in any way limiting its scope.

EXAMPLE 1 (IN ACCORDANCE WITH THE INVENTION)

Preparation of an EU-1 Zeolite Containing 2390 ppm by Weight of Sodium

The starting material used was an as-synthesized EU-1 zeolite comprising the organic template, namely 1,6 N,N,N',N',N'-hexamethylhexamethylene diammonium, and with an overall Si/Al atomic ratio of 14.4 and a sodium content by weight of 2390 ppm by weight, corresponding to an Na/Al atomic ratio (%) of 9.7. This zeolite was synthesized in accordance with the disclosure in patent EP-B1-0 042 226. To prepare such a zeolite, the reaction mixture had the following molar composition:

60 $SiO_2$: 10.6 $Na_2O$: 5.27 NaBr: 1.5 $Al_2O_3$: 19.5 Hexa-$Br_2$: 2777 $H_2O$.

Hexa-$Br_2$ is 1,6 N,N,N,N',N',N'-hexamethylhexamethylene diammonium, with the bromine as the counter-ion. The reaction mixture was placed in an autoclave, with stirring (300 rpm), for 5 days at 180° C. This EU-1 zeolite underwent dry calcining at 550° C. in a stream of dry air for 24 hours in order to eliminate the organic template. The solid obtained was given the reference EU-1(1) and had an overall Si/Al atomic ratio of 14.4 and a Na/Al atomic ratio of 9.7%.

EXAMPLE 2 (NOT IN ACCORDANCE WITH THE INVENTION)

Preparation of an EU-1 Zeolite Containing 210 ppm by Weight of Sodium

The starting material used was an as-synthesized EU-1 zeolite comprising the organic template, namely 1,6 N,N,N',N',N'-hexamethylhexamethylene diammonium, and with an overall Si/Al atomic ratio of 14.4 and a sodium content by weight of 210 ppm by weight, corresponding to an Na/Al atomic ratio (%) of 0.85. This zeolite was synthesized in accordance with the disclosure in patent EP-B1-0 042 226. To prepare such a zeolite, the reaction mixture had the following molar composition:

60 $SiO_2$: 10.6 $Na_2O$: 5.27 NaBr: 1.5 $Al_2O_3$: 19.5 Hexa-$Br_2$: 2777 $H_2O$.

Hexa-$Br_2$ is 1,6 N,N,N,N',N',N'-hexamethylhexamethylene diammonium, with the bromine as the counter-ion. The reaction mixture was placed in an autoclave, with stirring (300 rpm), for 5 days at 180° C. This EU-1 zeolite initially underwent dry calcining at 550° C. in a stream of dry air for 24 hours in order to eliminate the organic template. Next, the solid obtained underwent four ion exchanges in a 10N $NH_4NO_3$ solution, at approximately 100° C. for 4 hours for each exchange. The solid obtained was given the reference EU-1(2) and had an overall Si/Al atomic ratio of 14.4 and a Na/Al atomic ratio of 0.85%.

EXAMPLE 3 (NOT IN ACCORDANCE WITH THE INVENTION)

Preparation of an EU-1 Zeolite Containing 5900 ppm by Weight of Sodium

The starting material used was an as-synthesized EU-1 zeolite comprising the organic template, namely 1,6 N,N,N,N',N',N'-hexamethylhexamethylene diammonium, and with an overall Si/Al atomic ratio of 14.4 and a sodium content by weight of 5900 ppm by weight, corresponding to an Na/Al atomic ratio (%) of 23.9. This zeolite was synthesized in accordance with the disclosure in patent EP-B1-0 042 226. To prepare such a zeolite, the reaction mixture had the following molar composition:

60 $SiO_2$: 10.6 $Na_2O$: 5.27 NaBr: 1.5 $Al_2O_3$: 19.5 Hexa-$Br_2$: 2777 $H_2O$.

Hexa-$Br_2$ is 1,6 N,N,N,N',N',N'-hexamethylhexamethylene diammonium, with the bromine as the counter-ion. The reaction mixture was placed in an autoclave, with stirring (300 rpm), for 5 days at 180° C. This EU-1 zeolite initially underwent dry calcining at 550° C. in a stream of dry air for 24 hours in order to eliminate the organic template. Next, the solid obtained underwent four ion exchanges in a 10N $NH_4NO_3$ solution, at approximately 100° C. for 4 hours for each exchange. The zeolite was then back-exchanged with sodium in a sodium nitrate solution at ambient temperature for 4 hours in order to obtain a Na/Al ratio of 23.9% by mole. The solid obtained was given the reference EU-1(3) and had an overall Si/Al atomic ratio of 14.4 and a Na/Al atomic ratio of 23.9%.

EXAMPLE 4 (IN ACCORDANCE WITH THE INVENTION)

Preparation of Catalyst A Comprising an EU-1 Zeolite Containing 2390 ppm of Sodium (Na/Al=9.7% by Mole)

The EU-1 (1) zeolite obtained in Example 1 was then shaped by extrusion with an alumina gel so that, after drying at a temperature of 100° C. overnight and calcining in dry air carried out at a temperature of 450° C. for 4 hours, the support S1 was obtained which contained 13% by weight of EU-1 zeolite and 87% of alumina. The alumina used had a sodium content of less than 20 ppm. This support S1 underwent anionic exchange with hexachloroplatinic acid in the presence of hydrochloric acid as a competing agent in order to deposit 1% by weight of platinum with respect to the weight of catalyst. The moist solid was then dried at 120° C. for 12 hours and calcined in a flow of dry air at a temperature of 500° C. for one hour. Catalyst A obtained contained, by weight, 13% of EU-1 zeolite, 86% by weight of alumina and 1% of platinum. Catalyst A contained approximately 310 ppm of sodium.

EXAMPLE 5 (NOT IN ACCORDANCE WITH THE INVENTION)

Preparation of Catalyst B Comprising an EU-1 Zeolite Containing 210 ppm of Sodium (Na/Al=0.85% by Mole)

The EU-1 (2) zeolite obtained in Example 2 was then shaped by extrusion with an alumina gel so that, after drying at a temperature of 100° C. overnight and calcining in dry air carried out at a temperature of 450° C. for 4 hours, the support S2 was obtained which contained 13% by weight of EU-1 zeolite and 87% of alumina. The alumina used had a sodium content of less than 20 ppm. This support S2 underwent anionic exchange with hexachloroplatinic acid in the presence of hydrochloric acid as a competing agent in order to deposit 1% by weight of platinum with respect to the weight of catalyst. The moist solid was then dried at 120° C. for 12 hours and calcined in a flow of dry air at a temperature of 500° C. for one hour. Catalyst B obtained contained, by weight, 13% of EU-1 zeolite, 86% by weight of alumina and 1% of platinum. Catalyst B contained approximately 27 ppm of sodium.

EXAMPLE 6 (NOT IN ACCORDANCE WITH THE INVENTION)

Preparation of Catalyst C Comprising an EU-1 Zeolite Containing 5590 ppm of Sodium (Na/Al=23.9% by Mole)

The EU-1 (3) zeolite obtained in Example 3 was then shaped by extrusion with an alumina gel so that, after drying at a temperature of 100° C. overnight and calcining in dry air carried out at a temperature of 450° C. for 4 hours, the support S3 was obtained which contained 13% by weight of EU-1 zeolite and 87% of alumina. The alumina used had a sodium content of less than 20 ppm. This support S3 underwent anionic exchange with hexachloroplatinic acid in the presence of hydrochloric acid as a competing agent in order to deposit 1% by weight of platinum with respect to the weight of catalyst. The moist solid was then dried at 120° C. for 12 hours and calcined in a flow of dry air at a temperature of 500° C. for one hour. Catalyst C obtained contained, by weight, 13% of EU-1 zeolite, 86% by weight of alumina and 1% of platinum. Catalyst C contained approximately 770 ppm of sodium.

EXAMPLE 7

Evaluation of Catalytic Properties of Catalysts A, B and C in the Isomerization of Ethylbenzene The feed to be isomerized, brought into contact with catalysts A, B and C, was solely constituted by ethylbenzene.

The isomerization operating conditions were as follows:
temperature: 410° C.;
total pressure: 10 bar (1 bar=0.1 MPa);
partial pressure of hydrogen: 8 bar;
feed: ethylbenzene;
hourly space velocity, expressed as kilograms of feed introduced per kilogram of catalyst per hour, equal to 8.7 $h^{-1}$.

The catalytic properties of catalysts A, B and C were evaluated for the isomerization of ethylbenzene. Each of catalysts A, B and C was reduced in hydrogen for 4 hours at 480° C. before injecting the feed.

The catalysts were compared in terms of activity (by approach to equilibrium of para-xylene and by ethylbenzene conversion).

In order to calculate the approach to equilibrium of para-xylene (AEQ pX), the concentration of para-xylene (% pX) is expressed with respect to the three xylene isomers.

The approach to equilibrium of para-xylene (AEQ pX) is defined as follows:

$$AEQ\ pX(\%)=100\times(\%\ pX_{effluent}-\%\ pX_{feed})/(\%\ pX_{equilibrium}-\%\ pX_{feed})$$

The ethylbenzene conversion, Cv EB(%), is defined as follows:

Cv EB(%)=100×(% EB$_{feed}$−% EB$_{effluent}$)/% EB$_{feed}$

The results obtained under the same operating conditions are presented in Table 1.

TABLE 1

Activity of catalysts A, B and C after 4000 min of reaction

| Activity (%) | Catalyst A | Catalyst B | Catalyst C |
|---|---|---|---|
| AEQ pX | 96.7 | 96.8 | 96.6 |
| Cv EB | 30.4 | 26.1 | 24.3 |

The results presented in Table 1 show that catalyst A with a sodium content of 310 ppm prepared in accordance with the invention results in better catalytic performance in terms of ethylbenzene conversion activity than those obtained from catalysts B and C, not in accordance with the invention.

The entire disclosures of all applications, patents and publications, cited herein and of corresponding French Application No. 12/03064, filed Nov. 15, 2012 are incorporated by reference herein.

The invention claimed is:

1. A process for isomerizing an aromatic cut containing at least one aromatic compound containing 8 carbon atoms per molecule to produce p-xylene, comprising contacting the aromatic cut with a catalyst comprising a support and wherein the support comprises at least one zeolite with structure type EUO,
   wherein a method of preparing the catalyst comprises:
   obtaining the at least one zeolite with structure type EUO having an overall Si/Al atomic ratio of 5 to 45, a sodium content of 1000 to 3000 ppm by weight, and a Na/Al ratio of 5% to 15% by mole, and
   performing steps i) and ii) in either order such that the catalyst contains a final sodium content of 75 to 600 ppm by weight:
   i) preparing the support by mixing the at least one zeolite with a matrix such that a zeolite content is from 8% to 15% by weight with respect to the support; and
   ii) depositing at least one metal from group VIII of the periodic table of the elements onto the support or onto the at least one zeolite.

2. A process according to claim 1, in which the at least one zeolite with structure type EUO before steps i) and ii) has a Si/Al ratio of 10 to 40.

3. A process according to claim 1, in which the catalyst contains a final sodium content of 150 to 500 ppm by weight.

4. A process according to claim 1, in which the at least one zeolite with structure type EUO before steps i) and ii) is obtained by synthesis or is purchased commercially.

5. A process according to claim 1, in which the at least one zeolite with structure type EUO before steps i) and ii) has previously undergone one or more ion exchange(s) in order to obtain the characteristics required in step i).

6. A process according to claim 5, in which the at least one zeolite is pre-calcined before undergoing the one or more ion exchanges(s).

7. A process according to claim 1, in which the at least one zeolite with structure type EUO is EU-1 zeolite, ZSM-50 zeolite or TPZ-3 zeolite.

8. A process according to claim 1, in which the at least one zeolite with structure type EUO is EU-1 zeolite.

9. A process according to claim 1, in which the matrix is selected from the group consisting of clays, magnesia, aluminas, silicas, titanium oxide, boron oxide, zirconia, aluminum phosphates, titanium phosphates, zirconium phosphates, silica-alumina, charcoal, and a mixture of at least two of these.

10. A process according to claim 1, in which the matrix is an alumina.

11. A process according to claim 1, in which the matrix contains sodium content of less than 2000 ppm.

12. A process according to claim 1, in which the catalyst also comprises at least one metal selected from groups IIIA or IVA of the periodic table of the elements.

13. A process according to claim 1, in which step i) for preparing the support is followed by oven drying carried out at a temperature of 100° C. to 150° C. for a period of 5 to 20 hours followed by calcining carried out at a temperature of 250° C. to 600° C. for a period of 1 to 8 hours.

14. A process according to claim 1 in which, before carrying out the isomerization process, the method of preparing the catalyst is terminated by calcining at a temperature of 250° C. to 600° C. for a period of 0.5 to 10 hours preceded by drying at a temperature from ambient temperature to 250° C.

15. A process according to claim 1, in which prior reduction of the catalyst is carried out ex situ or in situ in a stream of hydrogen at a temperature of 450° C. to 600° C., for a period of 0.5 to 4 hours before carrying out the isomerization process.

16. A process according to claim 1, in which the aromatic cut comprises a mixture of xylenes, ethylbenzene, or a mixture thereof.

17. A process according to claim 1, in which the isomerization is carried out at a temperature of 300° C. to 500° C., a partial pressure of hydrogen of 0.3 to 1.5 MPa, a total pressure of 0.45 to 1.9 MPa, and at an hourly space velocity, expressed in kilograms of feed introduced per kilogram of catalyst per hour, of 0.25 to 30 h$^{-1}$.

18. A process according to claim 1, in which the at least one zeolite with structure type EUO before steps i) and ii) has a Si/Al atomic ratio of 10 to 25.

19. A process according to claim 1, in which the matrix contains sodium in a sodium content of less than 200 ppm.

* * * * *